US009561217B2

(12) United States Patent
Kiyonaka et al.

(10) Patent No.: US 9,561,217 B2
(45) Date of Patent: *Feb. 7, 2017

(54) PHARMACEUTICAL COMPOSITION CONTAINING AS AN ACTIVE INGREDIENT 5-METHYL-1-PHENYL-2-(1H)-PYRIDONE

(71) Applicant: INTERMUNE, INC., Brisbane, CA (US)

(72) Inventors: Gakuji Kiyonaka, Amagasaki (JP); Yoshihiro Furuya, Amagasaki (JP); Yusuke Suzuki, Amagasaki (JP)

(73) Assignee: INTERMUNE, INC., Brisbane, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/951,313

(22) Filed: Nov. 24, 2015

(65) Prior Publication Data
US 2016/0074375 A1 Mar. 17, 2016

Related U.S. Application Data

(63) Continuation of application No. 14/671,251, filed on Mar. 27, 2015, now abandoned, which is a continuation of application No. 13/662,221, filed on Oct. 26, 2012, now Pat. No. 9,017,722, which is a continuation of application No. 13/333,142, filed on Dec. 21, 2011, now abandoned, which is a continuation of application No. 12/941,994, filed on Nov. 8, 2010, now abandoned, which is a continuation of application No. 10/470,334, filed as application No. PCT/JP02/00544 on Jan. 25, 2002, now Pat. No. 7,867,516.

(30) Foreign Application Priority Data

Jan. 29, 2001 (JP) ................................. 2001-019393

(51) Int. Cl.
A61K 31/4418 (2006.01)
A61K 9/28 (2006.01)
A61K 9/20 (2006.01)
A61K 31/4412 (2006.01)
C07D 213/64 (2006.01)

(52) U.S. Cl.
CPC ......... A61K 31/4418 (2013.01); A61K 9/2018 (2013.01); A61K 9/2054 (2013.01); A61K 9/28 (2013.01); A61K 9/282 (2013.01); A61K 9/2813 (2013.01); A61K 9/2866 (2013.01); A61K 31/4412 (2013.01); C07D 213/64 (2013.01)

(58) Field of Classification Search
None
See application file for complete search history.

(56) References Cited

U.S. PATENT DOCUMENTS 3,974,281 A 8/1976 Gadekar
4,042,699 A 8/1977 Gadekar
4,052,509 A 10/1977 Gadekar
4,753,801 A * 6/1988 Oren ...................... A61K 31/19 424/465
5,310,562 A * 5/1994 Margolin ................ A61K 31/44 424/423
5,518,729 A 5/1996 Margolin
5,591,766 A * 1/1997 Bang .................. A61K 31/4375 514/412
5,641,536 A * 6/1997 Lech .................... A61K 9/2826 427/2.14
5,681,382 A 10/1997 Kokubo
5,716,632 A 2/1998 Margolin
6,090,822 A 7/2000 Margolin
6,299,904 B1 10/2001 Shimizu et al.
6,300,349 B1 10/2001 Margolin
6,328,994 B1 12/2001 Shimizu et al.
7,767,225 B2 8/2010 Radhakrishnan et al.
7,825,133 B2 11/2010 Yi
7,867,516 B2 1/2011 Kiyonaka et al.
7,988,994 B2 8/2011 Radhakrishnan et al.
8,383,150 B2 2/2013 Radhakrishnan et al.
8,753,679 B2 6/2014 Radhakrishnan et al.
9,017,722 B2 4/2015 Kiyonaka et al.
2003/0104066 A1 6/2003 Murai et al.
2004/0006091 A1 1/2004 Kyle et al.
2004/0044003 A1 3/2004 Kyle et al.

(Continued)

FOREIGN PATENT DOCUMENTS

EP 0173516 A2 3/1986
EP 0383591 A2 8/1990

(Continued)

OTHER PUBLICATIONS

"Jitsuyou lyakuhin Tenkabutu", Kabushiki Gaishya Kagaku Kougyou Shya, pp. 104-13 (Mar. 5, 1974).
"Phase II Trial of Pirfenidone in Children, Adolescents, and Young Adults with Neurofibromatosis Type I and Progressive Plexiform Neurofibromas," NIH Clinical Research Studies, Protocol No. 04-C-0080 (Last Update: Feb. 28, 2009).
Azuma et al., "Double-blind, Placebo-controlled Trial of Pirfenidone in Patients with Idiopathic Pulmonary Fibrosis," Am J. Respir. Crit. Care Med. 171: 1040-47 (2005).
Cain et al., Inhabition of tumor necrosis factor and subsequent endotoxin shock by pirfenidone. Int. J. Immunopharmacol. 20: 685-95 (1998).
Combined PCT Search Report and Written Opinion, PCT/US2006/037057 (Apr. 23, 2007).
Decision of Rejection, Chinese patent application No. 2006/0034874.2, mailed Apr. 1, 2012.
Decision on Grant, Ukrainian patent application No. 2008 05048, Nov. 22, 2011.
Examination Report, ARIPO patent application No. AP/P/2008/004390, dated Aug. 11, 2011.
Examination Report, ARIPO patent application No. AP/P/2008/004390, dated Nov. 7, 2012.

(Continued)

Primary Examiner — Jianfeng Song
(74) Attorney, Agent, or Firm — Marshall, Gerstein & Borun LLP

(57) ABSTRACT

A tablet characterized by comprising 5-methyl-1-phenyl-2-(1H)-pyridone as the main ingredient and, based on the main ingredient, 10 to 50 wt. % excipient, 5 to 40 wt. % disintegrator, 1 to 10 wt. % binder, 0.5 to 5 wt. % lubricant, 2 to 6 wt. % coating basis, and 0.05 to 3 wt. % light-shielding agent, wherein the odor or bitterness of the 5-methyl-1-phenyl-2-(1H)-pyridone is masked and the light stability is improved.

20 Claims, No Drawings

(56) References Cited

U.S. PATENT DOCUMENTS

| | | |
|---|---|---|
| 2004/0048902 A1 | 3/2004 | Kiyonaka et al. |
| 2004/0106625 A1 | 6/2004 | Kyle et al. |
| 2005/0059671 A1 | 3/2005 | Sun et al. |
| 2005/0245500 A1 | 11/2005 | Roth et al. |
| 2005/0267093 A1 | 12/2005 | Lehmann-Lintz et al. |
| 2006/0128717 A1 | 6/2006 | Sun et al. |
| 2006/0199824 A1 | 9/2006 | Sun et al. |
| 2006/0258669 A1 | 11/2006 | Kyle et al. |
| 2007/0054842 A1 | 3/2007 | Blatt et al. |
| 2009/0170867 A1 | 7/2009 | Kurose |
| 2009/0170868 A1 | 7/2009 | Tafesse |
| 2009/0176796 A1 | 7/2009 | Tafesse |
| 2010/0120862 A1 | 5/2010 | Tafesse |
| 2010/0130499 A1 | 5/2010 | Tafesse |
| 2010/0137306 A1 | 6/2010 | Tafesse |
| 2011/0053950 A1 | 3/2011 | Meyers et al. |
| 2011/0104276 A1 | 5/2011 | Kiyonaka et al. |
| 2012/0183615 A1 | 7/2012 | Kiyonaka et al. |
| 2013/0115288 A1 | 5/2013 | Kiyonaka et al. |
| 2015/0209341 A1 | 7/2015 | Kiyonaka et al. |

FOREIGN PATENT DOCUMENTS

| | | |
|---|---|---|
| EP | 0458861 A1 | 12/1991 |
| EP | 0837052 A1 | 4/1998 |
| EP | 0901787 A1 | 3/1999 |
| EP | 1138329 A2 | 10/2001 |
| EP | 1319409 A1 | 6/2003 |
| EP | 1356816 A1 | 10/2003 |
| EP | 1757591 A1 | 2/2007 |
| EP | 2261218 A2 | 12/2010 |
| WO | WO-90/09176 A1 | 8/1990 |
| WO | WO-94/26249 A1 | 11/1994 |
| WO | WO-96/01820 A1 | 1/1996 |
| WO | WO-96/11210 A1 | 4/1996 |
| WO | WO-97/10712 A1 | 3/1997 |
| WO | WO-97/41830 A1 | 11/1997 |
| WO | WO-01/66551 A2 | 9/2001 |
| WO | WO-02/08221 | 1/2002 |
| WO | WO-02/083134 A1 | 10/2002 |
| WO | WO-02/087549 A1 | 11/2002 |
| WO | WO-03/045313 A2 | 6/2003 |
| WO | WO-03/066595 A2 | 8/2003 |
| WO | WO-03/074520 A1 | 9/2003 |
| WO | WO-2004/002983 A2 | 1/2004 |
| WO | WO-2004/011441 A1 | 2/2004 |
| WO | WO-2004/019758 A2 | 3/2004 |
| WO | WO-2004/019863 A2 | 3/2004 |
| WO | WO-2004/029031 A2 | 4/2004 |
| WO | WO-2004/035549 A1 | 4/2004 |
| WO | WO-2004/058754 A1 | 7/2004 |
| WO | WO-2004/087126 A1 | 10/2004 |
| WO | WO-2004/100944 A1 | 11/2004 |
| WO | WO-2004/103296 A2 | 12/2004 |
| WO | WO-2005/004763 A1 | 1/2005 |
| WO | WO-2005/004866 A1 | 1/2005 |
| WO | WO-2005/009987 A1 | 2/2005 |
| WO | WO-2005/009988 A1 | 2/2005 |
| WO | WO-2005/012287 A1 | 2/2005 |
| WO | WO-2005/016241 A2 | 2/2005 |
| WO | WO-2005/030753 A2 | 4/2005 |
| WO | WO-2005/030766 A1 | 4/2005 |
| WO | WO-2005/040758 A2 | 5/2005 |
| WO | WO-2005/047256 A1 | 5/2005 |
| WO | WO-2005/066130 A1 | 7/2005 |
| WO | WO-2005/074899 A2 | 8/2005 |
| WO | WO-2005/079777 A1 | 9/2005 |
| WO | WO-2007/069773 A1 | 6/2007 |
| WO | WO-2008/132600 A2 | 11/2008 |
| WO | WO-2008/133973 A1 | 11/2008 |
| WO | WO-2009/147170 A2 | 12/2009 |
| WO | WO-2011/162409 A1 | 12/2011 |

OTHER PUBLICATIONS

Examination Report, Australian patent application No. 2006295440, dated Dec. 3, 2010.
Examination Report, Australian patent application No. 2011201520, dated Mar. 16, 2012.
Examination Report, Australian patent application No. 2013201986, dated May 3, 2013.
Examination Report, Australian patent application No. 2014240300, dated Nov. 21, 2014.
Examination Report, European Application No. 06815221.4, Dec. 9, 2011.
Examination Report, European Application No. 06815221.4, Oct. 25, 2010.
Examination Report, European Application No. 06815221.4, Sep. 26, 2012.
Examination Report, New Zealand patent application No. 565957, dated Mar. 13, 2012.
Examination Report, New Zealand patent application No. 565957, dated Mar. 24, 2011.
Examination Report, New Zealand patent application No. 565957, dated Sep. 22, 2011.
Examination Report, New Zealand patent application No. 565957, Jan. 14, 2010.
Examination Report, New Zealand patent application No. 591443, dated Dec. 6, 2012.
Examination Report, New Zealand patent application No. 591443, dated Jun. 22, 2012.
Examination Report, New Zealand patent application No. 591443, dated Mar. 8, 2011.
Examination Report, New Zealand patent application No. 591443, dated May 30, 2012.
Examination Report, New Zealand patent application No. 600129, dated May 30, 2012.
Examination Report, Nicaraguan National Phase Application No. 2008-000086, Jan. 18, 2013 (English translation).
Examination Report, Nicaraguan National Phase Application No. 2008/0086, Mar. 15, 2012 (English translation).
Examination Report, Philippines Application No. 1-2008-500545 (Sep. 21, 2011).
Examination Report, Vietnam patent application No. 1-2008-00880, Aug. 12, 2010.
Final office action, Japanese Patent Application No. 2008-532431 (May 2013).
First Examination Report, Indian Patent Application No. 2238/DELNP/2008, dated Sep. 18, 2013.
First Office Action, Chinese Patent Application No. 200680034874.2 dated Nov. 13, 2009.
First Office Action, Chinese patent application No. 201310343368.3, mailed Aug. 21, 2014.
First office action, Chinese patent application No. 20140057564.9, mailed Feb. 17, 2015.
Gahl et al., "Effect of Pirfenidone on the Pulmonary Fibrosis of Hermansky-Pudlak Syndrome," Molecular Genetics and Metabolism 76: 234-42 (2002).
Gennaro (ed.), Remington Farmacia, Tomo 2, Editorial Medica Panamericana, 19th ed. pp. 2485-9 (1995).
Georgian Search Report for corresponding Georgian Patent Application No. 10558/01 (Jun. 15, 2009).
InterMune, Dissolution Profile Comparison Study Report for Pirfenidone Capsules (2008).
International Preliminary Report on Patentability, PCT/US2006/037057 (Mar. 26, 2008).
Martinet et al., Exaggerated spontaneous release of platelet-derived growth factor by alveolar macrophages from patients with idiopathic pulmonary fibrosis. *N. Engl. J. Med.* 317: 202-9 (1987).
Nagai et al., Open-label compassionate use one year-treatment with pirfenidone to patients with chronic pulmonary fibrosis, *Intern. Med.* 41: 1118-23 (2002).
Notari, Biopharmaceutics and Clinical Pharmacokinetics: An Introduction, Marcel Dekker, Inc., New York and Basel, pp. 134-159 (4th ed. 1986).
Notice of Final Rejection, Korean patent application No. 10-2008-7006806, Dec. 23, 2013.

(56) References Cited

OTHER PUBLICATIONS

Notice of Final Rejection, Korean patent application No. 10-2013-7022095, Dec. 22, 2015.
Notice of Opposition to a European patent, European Patent No. EP1940364, Mar. 11, 2015.
Reply of the Patent Proprietor (Intermune) to the Notice of Opposition, European Patent No. EP1940364, Jun. 11, 2014.
Brief Communication of the Patent Proprietor (Intermune), Opposition Proceedings of European Patent No. EP1940364, Aug. 25, 2015.
Preliminary Non-binding Opinion of the Opposition Division, European Patent No. EP1940364, Oct. 28, 2015.
Notice of Reexamination, Chinese patent application No. 200680034874.2, mailed Apr. 23, 2013.
Office Action from Colombian patent application No. 08029322, completed Apr. 2012.
Office action, Canadian patent application No. 2,620,380 (Apr. 18, 2011).
Office Action, Canadian patent application No. 2,620,380, dated Sep. 13, 2011.
Office action, Canadian patent application No. 2,620,380, Sep. 20, 2010.
Office action, Canadian patent application No. 2,762,013, dated Dec. 17, 2012.
Office Action, Japanese Patent Application No. 2008-532431 (Apr. 17, 2012).
Office action, Korean patent application No. 10-2008-7006806 (Aug. 21, 2012).
Office Action, Korean patent application No. 10-2008-7006806, May 21, 2013.
Office Action, Korean patent application No. 10-2014-7004496, Dec. 21, 2015.
Office action, Mexican Patent Application No. MX/a/2008/003882 (Nov. 2010).
Office action, Vietnamese patent application No. 1-2008-00880 (Aug. 12, 2010).
Official Action, Eurasian patent application No. 200800881, dated Feb. 7, 2011.
Official Action, Eurasian patent application No. 200800881, dated Mar. 4, 2012.
Official Action, Japanese patent application No. 2008-532431, Mar. 18, 2015.
Official Action, Japanese patent application No. 2012-180913, Dec. 24, 2013.
Official Action, Japanese Patent Application No. 2014-129551, dated Jun. 1, 2015.
Official Action, Ukrainian patent application No. 2008 05048, dated Aug. 21, 2010.
Official Action, Uzebekistan patent application No. IAP 2008 0151, Apr. 13, 2009.
Official Action, Uzebekistan patent application No. IAP 2008 0151, Feb. 2011.
Official Action, Uzebekistan patent application No. IAP 2008 0151, Jul. 6, 2010.
Reason for Final Rejection, Japanese patent application No. 2012-180913, Oct. 8, 2014.
Reexamination Decision, Chinese patent application No. 200680034874.2, mailed Dec. 2, 2013.
Reexamination Notice, Chinese Patent Application No. 2006 80034874.2, Apr. 23, 2013.
Report on Deliberation Results, http://www.pmda.go.jp/english/service/pdf/Pirespa-Pirfenidone.pdf, (Sep. 2008).
Schmidt et al., Bioavailability of pirfenidone capsules following oral administration (human volunteers) (60-244-73). Affiliated Medical Research, Inc. Princeton, New Jersey (1974).
Search and Examination Report, Singapore patent application No. 200801941-6, Mar. 5, 2010.
Second Office Action, Chinese patent application No. 200680034874.2, mailed Mar. 30, 2011.
Second Office Action, Chinese patent application No. 201310343368.3, mailed Jul. 14, 2015.
Second office action, Chinese patent application No. 201410057564.9, mailed Jan. 8, 2016.
Shionogi & Co., Ltd., Pirespa® Tablet 200 mg Pirfenidone Tablet, Package Insert (Version 1, Oct. 2008) and English-language translation thereof.
Singapore Written Opinion (issued by the Danish Patent Ofifce) from corresponding Singaporean Patent Application No. 200801941-6 (Apr. 24, 2009).
Striker et al., Mesangial cell turnover: effect of heparin and peptide growth factor. *Lab Invest.* 64: 446-56 (1991).
Subsequent Substantive Examination Report, Philippines patent application No. 1/2008/500545, Aug. 15, 2014.
Subsequent Substantive Examination Report, Philippines patent application No. 1/2008/500545, Jun. 13, 2013.
Substantive Examination Report Stage 1, Indonesian application No. W-00200701530 (Mar. 2011).
U.S. Office Action, U.S. Appl. No. 10/470,334, mailed Aug. 22, 2006.
U.S. Office Action, U.S. Appl. No. 10/470,334, mailed Feb. 20, 2009.
U.S. Office Action, U.S. Appl. No. 10/470,334, mailed Jun. 26, 2008.
U.S. Office Action, U.S. Appl. No. 10/470,334, mailed May 11, 2007.
U.S. Office Action, U.S. Appl. No. 10/470,334, mailed Oct. 2, 2009.
U.S. Office Action, U.S. Appl. No. 12/067,712 (Nov. 15, 2010).
U.S. Office Action, U.S. Appl. No. 12/426,182 (Apr. 8, 2010).
U.S. Office Action, U.S. Appl. No. 12/426,182 (Nov. 18, 2009).
U.S. Office Action, U.S. Appl. No. 12/426,182 (Sep. 16, 2009).
U.S. Office Action, U.S. Appl. No. 12/941,994, mailed Jun. 23, 2011.
U.S. Office Action, U.S. Appl. No. 13/162,048, mailed Apr. 13, 2012.
U.S. Office Action, U.S. Appl. No. 13/333,142, mailed Apr. 27, 2012.
U.S. Office Action, U.S. Appl. No. 13/662,221, mailed Aug. 25, 2014.
U.S. Office Action, U.S. Appl. No. 13/662,221, mailed Jan. 24, 2014.
U.S. Office Action, U.S. Appl. No. 13/662,221, mailed Mar. 18, 2013.
U.S. Office Action, U.S. Appl. No. 14/271,720, mailed Apr. 23, 2015.
Van Barneveld et al., Natural course of bleomycin-induced pneumonitis . A follow-up study.*Am. Rev. Respir Dis.* 135: 48-51 (1987).
Zhang et al., Pirfenidone reduces firbonectin synthesis by cultured human retinal pigment epithelial cells. *Aust. N Z J. Ophthalmol.* 26: S74-6 (1998).
Report on Deliberation Results, http://www.pmda.go.jp/english/service/pdf/Pirespa-Pirfenidone.pdf (Sep. 16, 2008).

* cited by examiner

PHARMACEUTICAL COMPOSITION CONTAINING AS AN ACTIVE INGREDIENT 5-METHYL-1-PHENYL-2-(1H)-PYRIDONE

TECHNICAL FIELD

The present invention relates to a tablet containing as the main ingredient 5-methyl-1-phenyl-2-(1H)-pyridone.

BACKGROUND ART

5-Methyl-1-phenyl-2-(1H)-pyridone (nonproprietary name: pirfenidone) is a medicine for pulmonary fibrosis as indication. Various effects of pirfenidone have been reported, for example, 1) treating effect for fibrosis in lung, arteriosclerotic lesion, or the like is described in JP Laid-Open (Tokukai) No. H02-215719, 2) a similar effect to 1) of pirfenidone analogs is described in JP Laid-Open (Tokuhyo) No. H08-510251, 3) usefulness for treating inflammation in respiratory organs or cutis is described in U.S. Pat. No. 3,974,281, U.S. Pat. No. 4,042,699, and U.S. Pat. No. 4,052,509, and 4) inhibiting effect to the synthesis and release of TNF-α is described in JP Laid-Open (Tokuhyo) No. H11-512699.

In the above-mentioned 1) and 2), exemplified as a dosage form of pirfenidone are capsule, tablet, powder, granule, syrup, injection, cream, ointment, insufflation, eye lotion, suppository, and pill, preferable is capsule, injection, cream, and ointment, and working examples are only capsule and ointment. A tablet of pirfenidone and its preparation are not described concretely.

With regard to the dosage of pirfenidone, 600 mg to 2400 mg is administrated three times a day in above-mentioned 1). In test example 1 of 2), capsule containing 800 mg, 1200 mg, and 1600 mg of pirfenidone are described. In order to obtain a sufficient therapeutic effect, pirfenidone must be administrated much higher dose in comparison with a usual medicine.

In general, there are eight types of capsule: No. 000, 00, 0, 1, 2, 3, 4, and 5. The bigger the number is, the smaller the size is. The general amount of a medicine contained in each capsule depending on the bulk density or compressibility of the medicine, as follows: about 60 mg to 100 mg in No. 5 capsule, about 100 mg to 170 mg in No. 4 capsule, about 140 mg to 220 mg in No. 3 capsule, about 180 mg to 300 mg in No. 2 capsule, about 240 mg to 390 mg in No. 1 capsule, and about 340 mg to 540 mg in No. 0 capsule. While No. 2 to No. 4 capsules have often been used for administration to human, a smaller types such as No. 3 to No. 5 capsules are becoming more popular in light of easy administration. A capsule usually contains not only an active ingredient, but also a pharmaceutical additive such as excipient, binder, and disintegrator, for improving the stability and efficacy of the active ingredient.

For example, if the amount of pirfenidone per one dose is 600 mg as mentioned above, amount of granules or mixed powder of pirfenidone to be filled in a capsule is about 800 mg to 850 mg. In encapsulating such an amount a No. 000 capsule or two No. 0 capsules are needed, and a patient has a strong pain during the administration. In case of much higher dose, it is impossible to prepare a practical capsule

DISCLOSURE OF INVENTION

In General, a tablet is readily orally administrated than a capsule. The present inventors investigated a formulating of pirfenidone into a tablet which is considered to be effective to improve the compliance in oral administration of a high dose of pirfenidone. In the process, problems were found such as 1) a characteristic odor or bitterness of pirfenidone, 2) low compressibility of pirfenidone itself, and 3) light-stability.

In the above situation, the inventors of the present invention have prepared a pirfenidone tablet improved for the compliance, which masks its odor or bitterness, and has the light-stability and rapid dissolution rate, being compact and of sufficient hardness in spite of high content of the main ingredient, whereby accomplished the present invention.

That is, the present invention relates to the following.
1) A tablet containing as the main ingredient 5-methyl-1-phenyl-2-(1H)-pyridone.
2) A tablet as described in 1), the weight of which is 100 to 1000 mg.
3) A tablet as described in 1) or 2), which contains 10 to 85 wt. % the main ingredient to the weight of the tablet.
4) A tablet as described in any one of 1) to 3), wherein the content of the main ingredient is 200 mg to 400 mg.
5) A tablet as described in any one of 1) to 4), which contains a light-shielding agent.
6) A tablet as described in 5), which contains a 0.05 to 3 wt. % of the shielding agent based on the main ingredient.
7) A tablet as described in any one of 1) to 4), which contains 10 to 50 wt. % excipient, 5 to 40 wt. % disintegrator, 1 to 10 wt. % binder, 0.5 to 5 wt. % lubricant, 2 to 6 wt. % coating basis, and 0.05 to 3 wt. % light-shielding agent based on the main ingredient.
8) A tablet as described in 7), which contains 0.01 to 1 wt. % plasticizer based on the main ingredient.
9) A tablet as described in any one of 1) to 4), which consists of a plain tablet containing 10 to 50 wt. % excipient, 5 to 40 wt. % disintegrator, 1 to 10 wt. % binder, and 0.5 to 5 wt. % lubricant on the main ingredient, and coating layer containing 2 to 6 wt. % coating basis and 0.05 to 3 wt. % light-shielding agent based on the main ingredient.
10) A tablet as described in 9), which contains 0.01 to 1 wt. % plasticizer based on the main ingredient in a coating layer.
11) A tablet as described in any one of 1) to 4), which consists of a plain tablet containing 10 to 50 wt. % excipient selected from the group of lactose, corn starch, and crystalline cellulose, 5 to 40 wt. % disintegrator selected from the group of carmellose calcium, low substituted hydroxypropylcellulose, and cross-linked polyvinylpyrrolidone, 1 to 10 wt. % binder selected from the group of hydroxypropylcellulose and polyvinylpyrrolidone, and 0.5 to 5 wt. % lubricant selected from the group of magnesium stearate and talc on the main ingredient, and a coating layer containing 2 to 6 wt. % coating basis selected from the group of hydroxypropylmethylcellulose and hydroxypropylcellulose, 0.01 to 1 wt. % plasticizer selected from the group of triethyl citrate and triacetin, and 0.05 to 3 wt. % light-shielding agent selected from the group of titanium oxide and ferric oxide based on the main ingredient.
12) A tablet as described in 11), which consists of a plain tablet containing 10 to 50 wt. % lactose, 5 to 40 wt. % carmellose calcium, 1 to 10 wt. % hydroxypropylcellulose, and 0.5 to 5 wt. magnesium stearate on the main ingredient, and a coating layer containing 2 to 6 wt. % hydroxypropylmethylcellulose, 0.01 to 1 wt. % triethyl citrate and 0.05 to 3 wt % titanium oxide based on the main ingredient.
13) A tablet as described in any one of 1) to 4), which consists of a plain tablet containing 20 to 30 wt. % excipient selected from the group of lactose, corn starch, and crystalline cellulose, 7.5 to 15 wt. % disintegrator selected from the group of carmellose calcium, low substituted hydroxypropylcellulose, and cross-linked polyvinylpyrrolidone, 2 to 5 wt. % binder selected from the group of hydroxypropylcellulose and polyvinylpyrrolidone, and 0.5 to 3 wt. % lubricant selected from the group of magnesium stearate and talc on the main ingredient, and a coating layer containing 2 to 4 wt. % coating basis selected from the group of hydroxypropylmethylcellulose and hydroxypropylcellulose, 0.01 to 1 wt. % plasticizer selected from the group of triethyl citrate and triacetin, and 0.8 to 3 wt. % titanium oxide as a light-shielding agent based on the main ingredient.

14) A tablet as described in 13), which consists of a plain tablet containing 20 to 30 wt. % lactose, 7.5 to 15 wt. % carmellose calcium, 2 to 5 wt. % hydroxypropylcellulose, and 0.5 to 3 wt. magnesium stearate on the main ingredient, and a coating layer containing 2 to 4 wt. % hydroxypropylmethylcellulose, 0.01 to 1 wt. % triethyl citrate and 0.8 to 3 wt. % titanium oxide based on the main ingredient.

In the present specification, the term "excipient" means an excipient used in usual pharmaceutical preparations. Examples of the excipient include silicic acids such as light anhydrous silicic acid, synthetic aluminum silicate, and magnesium aluminometasilicate, inorganic salts such as calcium phosphate, calcium carbonate, and calcium sulfate, sugars such as lactose, sucrose, dextrose, mannitol, and sorbitol, starches such as corn starch, a starch, carboxymethyl starch, celluloses such as crystalline cellulose, and low substituted hydroxypropylcellulose, gum Arabic, dextran and pullulan. Lactose, corn starch, and crystalline cellulose are more preferable.

In the present specification, the term "disintegrator" means an additive agent which is used in order to disintegrate and disperse a tablet to minute particles t in the digestive organ. Examples of the disintegrator include corn starch, carboxymethylcellulose, carboxymethylcellulose calcium, low substituted hydroxypropylcellulose, carmellose sodium, crosscarmellose sodium, carboxymethylstarch sodium, and cross-linked polyvinylpyrrolidone. Carmellose calcium, low substituted hydroxypropylcellulose, cross-linked polyvinylpyrrolidone, and the like are more preferable.

In the present specification, the term "binder" means a binder used in usual pharmaceutical preparations. Examples of the binder include hydroxypropylcellulose, hydroxypropylmethylcellulose, and methylcellulose, polyvinylpyrrolidone. Hydroxypropylcellulose, polyvinylpyrrolidone, and the like are more preferable.

In the present specification, as "lubricant" are exemplified talc, calcium stearate, sodium stearate, and magnesium stearate. Magnesium stearate, talc, and the like are more preferable.

In the present specification, as "coating basis" are exemplified sucrose, talc, precipitated calcium carbonate, gelatin, gum Arabic, pullulan, hydroxypropylcellulose, hydroxypropylmethylcellulose, polyvinylacetal diethylaminoacetate, aminoalkyl methacrylate copolymer, cellulose acetate phthalate, methacrylic acid copolymer L, methacrylic acid copolymer LD, methacrylic acid copolymer S, hydroxypropylmethylcellulose phthalate, hydroxymethylpropylmethylcellulose acetate succinate, and carboxymethylethylcellulose. Hydroxypropylmethylcellulose, hydroxypropylcellulose, and the like are more preferable.

In the present specification, the term "light-shielding agent" means a light-shielding agent used in usual pharmaceutical preparations. Examples of the light-shielding agent include titanium oxide and ferric oxide. Titanium oxide, and the like are more preferable.

In the present specification, the term "plasticizer" means a plasticizer used in usual pharmaceutical preparations. Examples of the plasticizer include triethyl citrate, triacetin, glycerin fatty acid ester, and phthalic acid ester. Triethyl citrate, triacetin, and the like are more preferable.

BEST MODE FOR CARRYING OUT THE INVENTION

The present invention tablet is prepared in the following A) to D) processes.

A) A mixed powder containing pirfenidone, an excipient, and a disintegrator is granulated by spraying a binder with a fluid bed granulator to give granules.

B) The obtained granules are mixed with a disintegrator, a lubricant, and the like and is compressed at a force of 8 to 18 kN, preferably 11 to 15 kN to give pirfenidone plain tablets.

C) A coating solution containing a coating basis, a plasticizer (if necessary), and a light-shielding agent etc. is prepared.

D) The target pirfenidone tablet is obtained by coating the pirfenidone plain tablet obtained in B) with the above-mentioned coating solution.

In the above-mentioned processes, additives used in a usual solid preparation may be added appropriately.

The present invention relates to a tablet containing 5-methyl-1-phenyl-2-(1H)-pyridone as the main ingredient and preferable is a 100 to 1000 mg weight of tablet. 150 to 700 mg is more preferable and 240 to 480 mg is the most preferable. The amount of the active ingredient is preferably 10 to 85 wt. % the main ingredient to the tablet. 25 to 85 wt. % is more preferable and 50 to 85 wt. % is the most preferable. It is preferable that the content of the main ingredient is 200 mg to 400 mg.

The designed tablet is more compact, easier to take and contains a more amount of the main ingredient than capsule, thus effectively exhibiting the efficacy.

That is, the present invention tablet includes a more compact tablet than a capsule containing 5-methyl-1-phenyl-2-(1H)-pyridone as the main ingredient.

Further the present inventors have discovered the problem of light-stability of pirfenidone tablet in the preparation, and found a pirfenidone tablet improving the light-stability with a light-shielding agent. Furthermore they found preferable are a tablet including 0.05 to 3 wt. % light-shielding agent and a tablet including a light-shielding agent in the coating layer.

That is, the present invention tablet includes a tablet improving the light-stability and containing 5-methyl-1-phenyl-2-(1H)-pyridone as the main ingredient.

Preferable amounts of respective components except the main ingredient in a plain tablet are shown by wt. % to pirfenidone as the main ingredient. In consideration of the compliance, it is preferable that the amount of the other components is as small as possible because the amount of pirfenidone as the main ingredient is much. But the hardness of a tablet may decrease if the amounts of the other components are too little. An excipient is preferably a) 10 to 50 wt. %. b) 15 to 40 wt. % is more preferable. c) 20 to 30 wt. % is the most preferable. A disintegrator is preferably d) 5 to 40 wt. %. e) 5 to 25 wt. % is more preferable. f) 7.5 to 15 wt. % is the most preferable. A binder is preferably g) 1 to 10 wt. %. h) 1 to 7.5 wt. % is more preferable. i) 2 to 5 wt. % is the most preferable. A lubricant is preferably j) 0.5 to 5 wt. %. k) 0.5 to 4 wt. % is more preferable. l) 0.5 to 3 wt. % is the most preferable.

Preferable amounts of respective components in a coating solution are shown by wt. % to pirfenidone as the main ingredient. The components include a coating basis in order to mask a characteristic odor or bitter of pirfenidone, and a light-shielding agent to improve the light-stability, preferably that the amounts of while are as small as possible like the plain tablet. A coating basis is preferably in) 2 to 6 wt. %. n) 2 to 5 wt. % is more preferable. o) 2 to 4 wt. % is the most preferable. A light-shielding agent is preferably p) 0.05 to 3 wt. %. q) 0.05 to 2 wt. % is more preferable. r) 0.8 to 1.5 wt. % is the most preferable. A plasticizer is preferably s) not included or t) 0.05 to 1 wt. % if included.

Preferable amounts of the above-mentioned components to pirfenidone in the present invention tablet are shown as follows. That is, (excipient, disintegrator, binder, lubricant, coating basis, light-shielding agent, plasticizer)=(a, d, g, j, m, p, s), (a, d, g, j, m, p, t), (a, d, g, j, m, q, s), (a, d, g, j, m, q, t), (a, d, g, j, m, r, s), (a, d, g, j, m, r, t), (a, d, g, j, n, p, s), (a, d, g, j, n, p, t), (a, d, g, j, n, q, s), (a, d, g, j, n, q, t), (a, d, g, j, n, r, s), (a, d, g, j, n, r, t), (a, d, g, j, o, p, s), (a, d, g, j, o, p, t), (a, d, g, j, o, q, s), (a, d, g, j, o, q, t), (a, d, g, j, o, r, s), (a, d, g, j, o, r, t), (a, d, g, k, m, p, s), (a, d, g, k, m, p, t), (a, d, g, k, m, q, s), (a, d, g, k, m, q, t), (a, d, g, k, m, r, s), (a, d, g, k, m, r, t), (a, d, g, k, n, p, s), (a, d, g, k, n, p, t), (a, d, g, k, n, q, s), (a, d, g, k, n, q, t), (a, d, g, k, n, r, s), (a, d, g, k, n, r, t), (a, d, g, k, o, p, s), (a, d, g, k, o, p, t), (a, d, g, k, o, q, s), (a, d, g, k, o, q, t), (a, d, g, k, o, r, s), (a, d, g, k, o, r, t), (a, d, g, l, m, p, s), (a, d, g, l, m, p, t), (a, d, g, l, m, q, s), (a, d, g, l, m, q, t), (a, d, g, l, m, r, s), (a, d, g, l, m, r, t), (a, d, g, l, n, p, s), (a, d, g, l, n, p, t), (a, d, g, l, n, q, s), (a, d, g, l, n, q, t), (a, d, g, l, n, r, s), (a, d, g, l, n, r, t), (a, d, g, l, o, p, s), (a, d, g, l, o, p, t), (a, d, g, l, o, q, s), (a, d, g, l, o, q, t), (a, d, g, l, o, r, s), (a, d, g, l, o, r, t), (a, d, h, j, m, p, s), (a, d, h, j, m, p, t), (a, d, h, j, m, q, s), (a, d, h, j, m, q, t), (a, d, h, j, m, r, s), (a, d, h, j, m, r, t), (a, d, h, j, n, p, s), (a, d, h, j, n, p, t), (a, d, h, j, n, q, s), (a, d, h, j, n, q, t), (a, d, h, j, n, r, s), (a, d, h, j, n, r, t), (a, d, h, j, o, p, s), (a, d, h, j, o, p, t), (a, d, h, j, o, q, s), (a, d, h, j, o, q, t), (a, d, h, j, o, r, s), (a, d, h, j, o, r, t), (a, d, h, k, m, p, s), (a, d, h, k, m, p, t), (a, d, h, k, m, q, s), (a, d, h, k, m, q, t), (a, d, h, k, m, r, s), (a, d, h, k, m, r, t), (a, d, h, k, n, p, s), (a, d, h, k, n, p, t), (a, d, h, k, n, q, s), (a, d, h, k, n, q, t), (a, d, h, k, n, r, s), (a, d, h, k, n, r, t), (a, d, h, k, o, p, s), (a, d, h, k, o, p, t), (a, d, h, k, o, q, s), (a, d, h, k, o, q, t), (a, d, h, k, o, r, s), (a, d, h, k, o, r, t), (a, d, h, l, m, p, s), (a, d, h, l, m, p, t), (a, d, l, m, q, s), (a, d, h, l, m, q, t), (a, d, h, l, m, r, s), (a, d, h, l, m, r, t), (a, d, h, l, n, p, s), (a, d, h, l, n, p, t), (a, d, h, l, n, q, s), (a, d, h, l, n, q, t), (a, d, h, l, n, r, s), (a, d, h, l, n, r, t), (a, d, h, l, o, p, s), (a, d, h, l, o, p, t), (a, d, h, l, o, q, s), (a, d, h, l, o, q, t), (a, d, h, l, o, r, s), (a, d, h, l, o, r, t), (a, d, i, j, m, p, s), (a, d, i, j, m, p, t), (a, d, i, j, m, q, s), (a, d, i, j, m, q, t), (a, d, i, j, m, r, s), (a, d, j, m, r, t), (a, d, i, j, n, p, s), (a, d, i, j, n, p, t), (a, d, i, j, n, q, s), (a, d, i, j, n, q, t), (a, d, i, j, n, r s), (a, d, i, j, n, r, t), (a, d, i, j, o, p, s), (a, d, i, j, o, p, t), (a, d, i, j, o, q, s), (a, d, i, j, o, q, t), (a, d, i, j, o, r, s), (a, d, i, j, o, r, t), (a, d, i, k, m, p, s), (a, d, i, k, m, p, t), (a, d, i, k, m, q, s), (a, d, i, k, m, q, t), (a, d, i, k, m, r, s), (a, d, i, k, m, r, t), (a, d, i, k, n, p, s), (a, d, i, k, n, p, t), (a, d, i, k, n, q, s), (a, d, i, k, n, q, t), (a, d, i, k, n, r, s), (a, d, i, k, n, r, t), (a, d, i, k, o, p, s), (a, d, i, k, o, p, t), (a, d, i, k, o, q, s), (a, d, i, k, o, q, t), (a, d, i, k, o, r, s), (a, d, i, k, o, r, t), (a, d, i, l, m, p, s), (a, d, i, l, m, q, s), (a, d, i, l, m, q, t), (a, d, i, l, m, r, s), (a, d, i, l, m, r, t), (a, d, i, l, n, p, s), (a, d, i, l, n, p, t), (a, d, i, l, n, q, s), (a, d, i, l, n, q, t), (a, d, i, l, n, r, s), (a, d, i, l, n, r, t), (a, d, i, l, o, p, s), (a, d, i, l, o, p, t), (a, d, i, l, o, q, s), (a, d, i, l, o, q, t), (a, d, i, l, o, r, s), (a, d, i, l, o, r, t), (a, e, g, j, m, p, s), (a, e, g, j, m, p, t), (a, e, g, j, m, q, s), (a, e, g, j, m, q, t), (a, e, g, j, m, r, s), (a, e, g, j, m, r, t), (a, e, g, j, n, p, s), (a, e, g, j, n, p, t), (a, e, g, j, n, q, s), (a, e, g, j, n, q, t), (a, e, g, j, n, r, s), (a, e, g, j, n, r, t), (a, e, g, j, o, p, s), (a, e, g, j, o, p, t), (a, e, g, j, o, q, s), (a, e, g, j, o, q, t), (a, e, g, j, o, r, s), (a, e, g, j, o, r, t), (a, e, g, k, m, p, s), (a, e, g, k, m, p, t), (a, e, g, k, m, q, s), (a, e, g, k, m, q, t), (a, e, g, k, m, r, s), (a, e, g, k, m, r, t), (a, e, g, k, n, p, s), (a, e, g, k, n, p, t), (a, e, g, k, n, q, s), (a, e, g, k, n, q, t), (a, e, g, k, n, r, s), (a, e, g, k, n, r, t), (a, e, g, k, o, p, s), (a, e, g, k, o, p, t), (a, e, g, k, o, q, s), (a, e, g, k, o, q, t), (a, e, g, k, o, r, s), (a, e, g, k, o, r, t), (a, e, g, l, m, p, s), (a, e, g, l, m, p, t), (a, e, g, l, m, q, s), (a, e, g, l, m, q, t), (a, e, g, l, m, r, s), (a, e, g, l, m, r, t), (a, e, g, l, n, p, s), (a, e, g, l, n, p, t), (a, e, g, l, n, q, s), (a, e, g, l, n, q, t), (a, e, g, l, n, r, s), (a, e, g, l, n, r, t), (a, e, g, l, o, p, s), (a, e, g, l, o, p, t), (a, e, g, l, o, q, s), (a, e, g, l, o, q, t), (a, e, g, l, o, r, s), (a, e, g, l, o, r, t), (a, e, h, j, m, p, s), (a, e, h, j, m, p, t), (a, e, h, j, m, q, s), (a, e, h, j, m, q, t), (a, e, h, j, m, r, s), (a, e, h, j, m, r, t), (a, e, h, j, n, p, s), (a, e, h, j, n, p, t), (a, e, h, j, n, q, s), (a, e, h, j, n, q, t), (a, e, h, j, n, r, s), (a, e, h, j, n, r, t), (a, e, h, j, o, p, s), (a, e, h, j, o, p, t), (a, e, h, j, o, q, s), (a, e, h, j, o, q, t), (a, e, h, j, o, r, s), (a, e, h, j, o, r, t), (a, e, h, k, m, p, s), (a, e, h, k, m, p, t), (a, e, h, k, m, q, s), (a, e, h, k, m, q, t), (a, e, h, k, m, r, s), (a, e, h, k, m, r, t), (a, e, h, k, n, p, s), (a, e, h, k, n, p, t), (a, e, h, k, n, q, s), (a, e, h, k, n, q, t), (a, e, h, k, n, r, s), (a, e, h, k, n, r, t), (a, e, h, k, o, p, s), (a, e, h, k, o, p, t), (a, e, h, k, o, q, s), (a, e, h, k, o, q, t), (a, e, h, k, o, r, s), (a, e, h, k, o, r, t), (a, e, h, l, m, p, s), (a, e, h, l, m, p, t), (a, e, h, l, m, q, s), (a, e, h, l, m, q, t), (a, e, h, l, m, r, s), (a, e, h, l, m, r, t), (a, e, h, l, n, p, s), (a, e, h, l, n, p, t), (a, h, l, n, q, s), (a, e, h, l, n, q, t), (a, e, h, l, n, r, s), (a, e, h, l, n, r, t), (a, e, h, l, o, p, s), (a, e, h, l, o, p, t), (a, e, h, l, o, q, s), (a, e, h, l, o, q, t), (a, e, h, l, o, r, s), (a, e, h, l, o, r, t), (a, e, i, j, m, p, s), (a, e, i, j, m, p, t), (a, e, i, j, m, q, s), (a, e, i, j, m, q, t), (a, e, i, j, m, r, s), (a, e, j, m, r, t), (a, e, i, j, n, p, s), (a, e, i, j, n, p, t), (a, e, i, j, n, q, s), (a, e, i, j, n, q, t), (a, e, i, j, n, r, s), (a, e, i, j, n, r, t), (a, e, i, j, o, p, s), (a, e, i, j, o, p, t), (a, e, i, j, o, q, s), (a, e, i, j, o, q, t), (a, e, i, j, o, r, s), (a, e, i, j, o, r, t), (a, e, i, k, m, p, s), (a, e, k, m, p, t), (a, e, i, k, m, q, s), (a, e, i, k, m, q, t), (a, e, i, k, m, r, s), (a, e, i, k, m, r, t), (a, e, i, k, n, p, s), (a, e, i, k, n, p, t), (a, e, i, k, n, q, s), (a, e, i, k, n, q, t), (a, e, i, k, n, r, s), (a, e, i, k, n, r, t), (a, e, i, k, o, p, s), (a, e, i, k, o, p, t), (a, e, i, k, o, q, s), (a, e, i, k, o, q, t), (a, e, i, k, o, r, s), (a, e, i, k, o, r, t), (a, e, i, l, m, p, s), (a, e, i, l, m, p, t), (a, e, i, l, m, q, s), (a, e, i, l, m, q, t), (a, e, i, l, m, r, s), (a, e, i, l, m, r, t), (a, e, i, l, n, p, s), (a, e, i, l, n, p, t), (a, e, i, l, n, q, s), (a, e, i, l, n, q, t), (a, e, i, l, n, r, s), (a, e, i, l, n, r, t), (a, e, i, l, o, p, s), (a, e, i, l, o, p, t), (a, e, i, l, o, q, s), (a, e, i, l, o, q, t), (a, e, i, l, o, r, s), (a, e, i, l, o, r, t), (a, f, g, j, m, p, s), (a, f, g, j, m, p, t), (a, f, g, j, m, q, s), (a, f, g, j, m, q, t), (a, f, g, j, m, r, s), (a, f, g, j, m, r, t), (a, f, g, j, n, p, s), (a, f, g, j, n, p, t), (a, f, g, j, n, q, s), (a, f, g, j, n, q, t), (a, f, g, j, n, r, s), (a, f, g, j, n, r, t), (a, f, g, j, o, p, s), (a, f, g, j, o, p, t), (a, f, g, j, o, q, s), (a, f, g, j, o, q, t), (a, f, g, j, o, r, s), (a, f, g, j, o, r, t), (a, f, g, k, m, p, s), (a, f, g, k, m, p, t), (a, f, g, k, m, q, s), (a, f, g, k, m, q, t), (a, f, g, k, m, r, s), (a, f, g, k, m, r, t), (a, f, g, k, n, p, s), (a, f, g, k, n, p, t), (a, f, g, k, n, q, s), (a, f, g, k, n, q, t), (a, f, g, k, n, r, s), (a, f, g, k, n, r, t), (a, f, g, k, o, p, s), (a, f, g, k, o, p, t), (a, f, g, k, a, q, s), (a, f, g, k, o, q, t), (a, f, g, k, o, r, s), (a, f, g, k, o, r, t), (a, f, g, l, m, p, s), (a, f, g, l, m, p, t), (a, f, g, l, m, q, s), (a, f, g, l, m, q, t), (a, f, g, l, m, r, s), (a, f, g, l, m, r, t), (a, f, g, l, n, p, s), (a, f, g, l, n, p, t), (a, f, g, l, n, q, s), (a, f, g, l, n, q, t), (a, f, g, l, n, r, s), (a, f, g, l, n, r, t), (a, f, g, l, o, p, s), (a, f, g, l, o, p, t), (a, f, g, l, o, q, s), (a, f, g, l, o, q, t), (a, f, g, l, o, r, s), (a, f, g, l, o, r, t), (a, f, h, j, m, p, s), (a, f, h, j, m, p, t), (a, f, h, j, m, q, s), (a, f, h, j, m, q, t), (a, f, h, j, m, r, s), (a, f, h, j, m, r, t), (a, f, h, j, n, p, s), (a, f, h, j, n, p, t), (a, f, h, j, n, q, s), (a, f, h, j, n, q, t), (a, f, h, j, n, r, s), (a, f, h, j, n, r, t), (a, f, h, j, o, p, s), (a, f, h, j, o, p, t), (a, f, h, j, o, q, s), (a, f, h, j, o, q, t), (a, f, h, j, o, r, s), (a, f, h, j, o, r, t), (a, f, h, k, m, p, s), (a, f, h, k, m, p, t), (a, f, h, k, m, q, s), (a, f, h, k, m, q, t), (a, f, h, k, m, r, s), (a, f, h, k, m, r, t), (a, f, h, k, n, p, s), (a, f, h, k, n, p, t), (a, f, h, k, n, q, s), (a, f, h, k, n, q, t), (a, f, h, k, n, r, s), (a, f, h, k, n, r, t), (a, f, h, k, o, p, s), (a, f, h, k, o, p, t), (a, f, h, k, o, q, s), (a, f, h, k, o, q, t), (a, f, h, k, o, r, s), (a, f, h, k, o, r, t), (a, f, h, l, m, p, s), (a, f, h, l, m, p, t), (a, f, h, l, m, q, s), (a, f, h, l, m, q, t), (a, f, h, l, m, r, s), (a, f, h, l, m, r, t), (a, f, h, l, n, p, s), (a, f, h, l, n, p, t), (a, f, h, l, n, q, s), (a, f, b, l, n, q, t), (a, f, h, l, n, r, s), (a, f, h, l, n, r, t), (a, f, h, l, o, p, s), (a, f, h, l, o, p, t), (a, f, h, l, o, q, s), (a, f, h, l, o, q, t), (a, f, h, l, o, r, s), (a, f, h, l, o, r, t), (a, f, i, j, m, p, s), (a, f, i, j, m, p, t), (a, f, i, j, m, q, s), (a, f, i, j, m, q, t), (a, f, i, j, m, r, s), (a, f, i, j, m, r, t), (a, f, i, j, n, p, s), (a, f, i, j, n, p, t), (a, f, i, j, n, q, s), (a, f, i, j, n, q, t), (a, f, i, j, n, r, s), (a, f, i, j, n, r, t), (a, f, i, j, o, p, s), (a, f, i, j, o, p, t), (a, f, i, j, o, q, s), (a, f, i, j, o, q, t), (a, f, i, j, o, r, s), (a, f, i, j, o, r, t), (a, f, i, k, m, p, s), (a, f, i, k, m, p, t), (a, f, i, k, m, q, s), (a, f, i, k, m, q, t), (a, f, i, k, m, r, s), (a, f, i, k, m, r, t), (a, f, i, k, n, p, s), (a, f, i, k, n, p, t), (a, f, i, k, n, q, s), (a, f, i, k, n, q, t), (a, f, i, k, n, r, s), (a, f, i, k, n, r, t), (a, f, i, k, o, p, s), (a, f, i, k, o, p, t), (a, f, i, k, o, q, s), (a, f, i, k, o, q, t), (a, f, i, k, o, r, s), (a, f, i, k, o, r, t), (a, f, i, l, m, p, s), (a, f, i, l, m, p, t), (a, f, i, l, m, q, s), (a, f, i, l, m, q, t), (a, f, i, l, m, r, s), (a, f, i, l, m, r, t), (a, f, i, l, n, p, s), (a, f, i, l, n, p, t), (a, f, i, l, n, q, s), (a, f, i, l, n, q, t), (a, f, i, l, n, r, s), (a, f, i, l, n, r, t), (a, f, i, l, o, p, s), (a, f, i, l, o, p, t), (a, f, i, l, o, q, s), (a, f, i, l, o, q, t), (a, f, i, l, o, r, s), (a, f, i, l, o, r, t), (b, d, g, j, m, p, s), (b, d, g, j, m, p, t), (b, d, g, j, m, q, s), (b, d, g, j, m, q, t), (b, d, g, j, m, r, s), (b, d, g, j, m, r, t), (b, d, g, j, n, p, s), (b, d, g, j, n, p, t), (b, d, g, j, n, q, s), (b, d, g, j, n, q, t), (b, d, g, j, n. r, s), (b, d, g, j, n, r, t), (b, d, g, j, o, p, s), (b, d, g, j, o, p, t), (b, d, g, j, o, q, s), (b, d, g, j, o, q, t), (b, d, g, j, o, r, s), (b, d, g, j, o, r, t), (b, d, g, k, m, p, s), (b, d, g, k, m, p, t), (b, d, g, k, m, q, s), (b, d, g, k, m, q, t), (b, d, g, k, m, r, s), (b, d, g, k, m, r, t), (b, d, g, k, n, p, s), (b, d, g, k, n, p, t), (b, d, g, k, n, q, s), (b, d, g, k, n, q, t), (b, d, g, k, n, r, s), (b, d, g, k, n, r, t), (b, d, g, k, o, p, s), (b, d, g, k, o, p, t), (b, d, g, k, o, q, s), (b, d, g, k, o, q, t), (b, d, g, k, o, r, s), (b, d, g, k, o, r, t), (b, d, g, l, m, p, s), (b, d, g, l, m, p, t), (b, d, g, l, m, q, s), (b, d, g, l, m, q, t), (b, d, g, l, m, r, s), (b, d, g, l, m, r, t), (b, d, g, l, n, p, s), (b, d, g, l, n, p, t), (b, d, g, l, n, q, s), (b, d, g, l, n, q, t), (b, d, g, l, n, r, s), (b, d, g, l, n, r, t), (b, d, g, l, o, p, s), (b, d, g, l, o, p, t), (b, d, g, l, o, q, s), (b, d, g, l, o, q, t), (b, d, g, l, o, r, s), (b, d, g, l, o, r, t), (b, d, h, j, m, p, s), (b, d, h, j, m, p, t), (b, d, h, j, m, q, s), (b, d, h, j, m, q, t), (b, d, h, j, m, r, s), (b, d, h, j, m, r, t), (b, d, h, j, n, p, s), (b, d, h, j, n, p, t), (b, d, h, j, n, q, s), (b, d, h, j, n, q, t), (b, d, h, j, n, r, s), (b, d, h, j, n, r, t), (b, d, h, j, o, p, s), (b, d, h, j, o, p, t), (b, d, h, j, o, q, s), (b, d, h, j, o, q, t), (b, d, h, j, o, r, s), (b, d, h, j, o, r, t), (b, d, h, k, m, p, s), (b, d, h, k, m, p, t), (b, d, h, k, m, q, s), (b, d, h, k, m, q, t), (b, d, h, k, m, r, s), (b, d, h, k, m, r, t), (b, d, h, k, n, p, s), (b, d, h, k, n, p, t), (b, d, h, k, n, q, s), (b, d, h, k, n, q, t), (b, d, h, k, n, r, s), (b, d, h, k, n, r, t), (b, d, h, k, o, p, s), (b, d, h, k, o, p, t), (b, d, h, k, o, q, s), (b, d, h, k, o, q, t), (b, d, h, k, o, r, s), (b, d, h, k, o, r, t), (b, d, h, l, m, p, s), (b, d, h, l, m, p, t), (b, d, h, l, m, q, s), (b, d, h, l, m, q, t), (b, d, h, l, m, r, s), (b, d, h, l, m, r, t), (b, d, h, l, n, p, s), (b, d, h, l, n, p, t), (b, d, h, l, n, q, s), (b, d, h, l, n, q, t), (b, d, h, l, n, r, s), (b, d, h, l, n, r, t), (b, d, h, l, o, p, s), (b, d, h, l, o, p, t), (b, d, h, l, o, q, s), (b, d, h, l, o, q, t), (b, d, h, l, o, r, s), (b, d, h, l, o, r, t), (b, d, h, l, o, r, t), (b, d, i, j, m, p, s), (b, d, i, j, m, p, t), (b, d, i, j, m, q, s), (b, d, i, j, m, q, t), (b, d, i, j, m, r, s), (b, d, i, j, m, r, t), (b, d, i, j, n, p, s), (b, d, i, j, n, p, t), (b, d, i, j, n, q, s), (b, d, i, j, n, q, t), (b, d, i, j, n, r, s), (b, d, i, j, n, r, t), (b, d, i, j, o, p, s), (b, d, i, j, o, p, t), (b, d, i, j, o, q, s), (b, d, i, j, o, q, t), (b, d, i, j, o, r, s), (b, d, i, j, o, r, t), (b, d, i, k, m, p, s), (b, d, i, k, m, p, t), (b, d, i, k, m, q, s), (b, d, i, k, m, q, t), (b, d, i, k, m, r, s), (b, d, i, k, m, r, t), (b, d, i, k, n, p, s), (b, d, i, k, n, p, t), (b, d, i, k, n, q, s), (b, d, i, k, n, q, t), (b, d, i, k, n, r, s), (b, d, i, k, n, r, t), (b, d, i, k, o, p, s), (b, d, i, k, o, p, t), (b, d, i, k, o, q, s), (b, d, i, k, o, q, t), (b, d, i, k, o, r, s), (b, d, i, k, o, r, t), (b, d, i, l, m, p, s), (b, d, i, l, m, p, t), (b, d, i, l, m, q, s), (b, d, i, l, m, q, t), (b, d, i, l, m, r, s), (b, d, i, l, m, r, t), (b, d, i, l, n, p, s), (b, d, i, l, n, p, t), (b, d, i, l, n, q, s), (b, d, i, l, n, q, t), (b, d, i, l, n, r, s), (b, d, i, l, n, r, t), (b, d, i, l, o, p, s), (b, d, i, l, o, p, t), (b, d, i, l, o, q, s), (b, d, i, l, o, q, t), (b, d, i, l, o, r, s), (b, d, i, l, o, r, t), (b, e, g, j, m, p, s), (b, e, g, j, m, p, t), (b, e, g, j, m, q, s), (b, e, g, j, m, q, t), (b, e, g, j, m, r, s), (b, e, g, j, m, r, t), (b, e, g, j, n, p, s), (b, e, g, j, n, p, t), (b, e, g, j, n, q, s), (b, e, g, j, n, q, t), (b, e, g, j, n, r, s), (b, e, g, j, n, r, t), (b, e, g, j, o, p, s), (b, e, g, j, o, p, t), (b, e, g, j, o, q, s), (b, e, g, j, o, q, t), (b, e, g, j, o, r, s), (b, e, g, j, o, r, t), (b, e, g, k, m, p, s), (b, e, g, k, m, p, t), (b, e, g, k, m, q, s), (b, e, g, k, m, q, t), (b, e, g, k, m, r, s), (b, e, g, k, m, r, t), (b, e, g, k, n, p, s), (b, e, g, k, n, p, t), (b, e, g, k, n, q, s), (b, e, g, k, n, q, t), (b, e, g, k, n, r, s), (b, e, g, k, n, r, t), (b, e, g, k, o, p, s), (b, e, g, k, o, p, t), (b, e, g, k, o, q, s), (b, e, g, k, o, q, t), (b, e, g, k, o, r, s), (b, e, g, k, o, r, t), (b, e, g, l, m, p, s), (b, e, g, l, m, p, t), (b, e, g, l, m, q, s), (b, e, g, l, m, q, t), (b, e, g, l, m, r, s), (b, e, g, l, m, r, t), (b, e, g, l, n, p, s), (b, e, g, l, n, p, t), (b, e, g, l, n, q, s), (b, e, g, l, n, q, t), (b, e, g, l, n, r, s), (b, e, g, l, n, r, t), (b, e, g, l, o, p, s), (b, e, g, l, o, p, t), (b, e, g, l, o, q, s), (b, e, g, l, o, q, t), (b, e, g, l, o, r, s), (b, e, g, l, o, r, t), (b, e, h, j, m, p, s), (b, e, h, j, m, p, t), (b, e, h, j, q, s), (b, e, h, j, m, q, t), (b, e, h, j, m, r, s), (b, e, h, j, m, r, t), (b, e, h, j, n, p, s), (b, e, h, j, n, p, t), (b, e, h, j, n, q, s), (b, e, h, j, n, q, t), (b, e, h, j, n, r, s), (b, e, h, j, n, r, t), (b, e, h, j, o, p, s), (b, e, h, j, o, p, t), (b, e, h, j, o, q, s), (b, e, h, j, o, q, t), (b, e, h, j, o, r, s), (b, e, h, j, o, r, t), (b, e, k, m, p, s), (b, e, h, k, m, p, t), (b, e, h, k, m, q, s), (b, e, h, k, m, q, t), (b, e, h, k, m, r, s), (b, e, h, k, m, r, t), (b, e, h, k, n, p, s), (b, e, h, k, n, p, t), (b, e, h, k, n, q, s), (b, e, h, k, n, q, t), (b, e, h, k, n, r, s), (b, e, h, k, n, r, t), (b, e, h, k, o, p, s), (b, e, h, k, o, p, t), (b, e, h, k, o, q, s), (b, e, h, k, o, q, t), (b, e, h, k, o, r, s), (b, e, h, l, m, p, s), (b, e, h, l, m, p, t), (b, e, h, l, m, q, s), (b, e, h, l, m, q, t), (b, e, h, l, m, r, s), (b, e, h, l, m, r, t), (b, e, h, l, n, p, s), (b, e, h, l, n, p, t), (b, e, h, l, n, q, s), (b, e, h, l, n, q, t), (b, e, h, l, n, r, s), (b, e, h, l, n, r, t), (b, e, h, l, o, p, s), (b, e, h, l, o, p, t), (b, e, h, l, o, q, s), (b, e, h, l, o, q, t), (b, e, h, l, o, r, s), (b, e, h, l, o, r, t), (b, e, i, j, m, p, s), (b, e, i, j, m, p, t), (b, e, i, j, m, q, s), (b, e, i, j, m, q, t), (b, e, i, j, m, r, s), (b, e, i, j, m, r, t), (b, e, i, j, n, p, s), (b, e, i, j, n, p, t), (b, e, i, j, n, q, s), (b, e, i, j, n, q, t), (b, e, i, j, n, r, s), (b, e, i, j, n, r, t), (b, e, i, j, o, p, s), (b, e, i, j, o, p, t), (b, e, i, j, o, q, s), (b, e, i, j, o, q, l), (b, e, i, j, o, r, s), (b, e, i, j, o, r, t), (b, e, i, k, m, p, s), (b, e, i, k, m, p, t), (b, e, i, k, m, q, s), (b, e, i, k, m, q, t), (b, e, i, k, m, r, s), (b, e, i, k, m, r, t), (b, e, i, k, n, p, s), (b, e, i, k, n, p, t), (b, e, i, k, n, q, s), (b, e, i, k, n, q, t), (b, e, i, k, n, r, s), (b, e, i, k, n, r, t), (b, e, i, k, o, p, s), (b, e, i, k, o, p, t), (b, e, i, k, o, q, s), (b, e, i, k, o, q, t), (b, e, i, k, o, r, s), (b, e, i, k, o, r, t), (b, e, i, l, m, p, s), (b, e, i, l, m, p, t), (b, e, i, l, m, q, s), (b, e, i, l, m, q, t), (b, e, i, l, m, r, s), (b, e, i, l, m, r, t), (b, e, i, l, n, p, s), (b, e, i, l, n, p, t), (b, e, i, l, n, q, s), (b, e, i, l, n, q, t), (b, e, i, l, n, r, s), (b, e, i, l, n, r, t), (b, e, i, l, o, p, s), (b, e, i, l, o, p, t), (b, e, i, l, o, q, s), (b, e, i, l, o, q, t), (b, e, i, l, o, r, s), (b, e, i, l, o, r, t), (b, f, g, j, m, p, s), (b, f, g, j, m, p, t), (b, f, g, j, m, q, s), (b, f, g, j, m, q, t), (b, f, g, j, m, r, s), (b, f, g, j, m, r, t), (b, f, g, j, n, p, s), (b, f, g, j, n, p, t), (b, f, g, j, n, q, s), (b, f, g, j, n, q, t), (b, f, g, j, n, r, s), (b, f, g, j, n, r, t), (b, f, g, j, o, p, s), (b, f, g, j, o, p, t), (b, f, g, j, o, q, s), (b, f, g, j, o, q, t), (b, f, g, j, o, r, s), (b, f, g, j, o, r, t), (b, f, g, k, m, p, s), (b, f, g, k, m, p, t), (b, f, g, k, m, q, s), (b, g, k, m, q, t), (b, f, g, k, m, r, s), (b, f, g, k, m, r, t), (b, g, k, n, p, s), (b, f, g, k, n, p, t), (b, f, g, k, n, q, s), (b, f, g, k, n, q, t), (b, f, g, k, n, r, s), (b, f, g, k, n, r, t), (b, f, g, k, o, p, s), (b, f, g, k, o, p, t), (b, f, g, k, o, q, s), (b, f, g, k, o, q, t), (b, f, g, k, o, r, s), (b, f, g, k, o, r, t), (b, f, g, l, m, p, s), (b, f, g, l, m, p, t), (b, f, g, l, m, q, s), (b, f, g, l, m, q, t), (b, f, g, l, m, r, s), (b, f, g, l, m, r, t), (b, f, g, l, n, p, s), (b, f, g, l, n, p, t), (b, f, g, l, n, q, s), (b, f, g, l, n, q, t), (b, f, g, l, n, r, s), (b, f, g, l, n, r, t), (b, f, g, l, o, p, s), (b, f, g, l, o, p, t), (b, f, g, l, o, q, s), (b, f, g, l, o, q, t), (b, f, g, l, o, r, s), (b, f, g, l, o, r, t), (b, f, h, j, m, p, s), (b, f, h, j, m, p, t), (b, f, h, j, m, q, s), (b, f, h, j, m, q, t), (b, f, h, j, m, r, s), (b, f, h, j, m, r, t), (b, f, h, j, n, p, s), (b, f, h, j, n, p, t), (b, f, h, j, n, q, s), (b, f, h, j, n, q, t), (b, f, h, j, n, r, s), (b, f, h, j, n, r, t), (b, f, h, j, o, p), (b, f, h, j, o, p, t), (b, f, h, j, o, q, s), (b, f, h, j, o, q, t), (b, f, h, j, o, r, s), (b, f, h, j, o, r, t), (b, f, h, k, m, p, s), (b, f, h, k, m, p, t), (b, f, h, k, m, q, s), (b, f, h, k, m, q, t), (b, f, h, k, m, r, s), (b, f, h, k, m, r, t), (b, f, h, k, n, p, s), (b, f, h, k, n, p, t), (b, f, h, k, n, q, s), (b, f, h, k, n, q, t), (b, f, h, k, n, r, s), (b, f, h, k, n, r, t), (b, f, h, k, o, p, s), (b, f, h, k, o, p, t), (b, f, h, k, o, q, s), (b, f, h, k, o, q, t), (b, f, h, k, o, r, s), (b, f, h, k, o, r, t), (b, f, h, l, m, p, s), (b, f, h, l, m, p, t), (b, f, h, l, m, q, s), (b, f, h, l, m, q, t), (b, f, h, l, m, r, s), (b, f, h, l, m, r, t), (b, f, h, l, n, p, s), (b, f, h, l, n, p, t), (b, f, h, l, n, q, s), (b, f, h, l, n, q, t), (b, f, h, l, n, r, s), (b, f, h, l, n, r, t), (b, f, h, l, o, p, s), (b, f, h, l, o, p, t), (b, f, h, l, o, q, s), (b, f, h, l, o, q, t), (b, f, h, l, o, r, s), (b, f, h, l, o, r, t), (b, f, i, j, m, p, s), (b, f, i, j, m, p, t), (b, f, i, j, m, q, s), (b, f, i, j, m, q, t), (b, f, i, j, m, r, s), (b, f, i, j, m, r, t), (b, f, i, j, n, p, s), (b, f, i, j, n, p, t), (b, f, i, j, n, q, s), (b, f, i, j, n, q, t), (b, f, i, j, n, r, s), (b, f, i, j, n, r, t), (b, f, i, j, o, p, s), (b, f, i, j, o, p, t), (b, f, i, j, o, q, s), (b, f, i, j, o, q, t), (b, f, i, j, o, r, s), (b, f, i, j, o, r, t), (b, f, i, k, m, p, s), (b, f, i, k, m, p, t), (b, f, i, k, m, q, s), (b, f, i, k, m, q, t), (b, f, i, k, m, r, s), (b, f, i, k, m, r, t), (b, f, i, k, n, p, s), (b, f, i, k, n, p, t), (b, f, i, k, n, q, s), (b, f, i, k, n, q, t), (b, f, i, k, n, r, s), (b, f, i, k, n, r, t), (b, f, i, k, o, p, s), (b, f, i, k, o, p, t), (b, f, i, k, o, q, s), (b, f, i, k, o, q, t), (b, f, i, k, o, r, s), (b, f, i, l, m, p, s), (b, f, i, l, m, p, t), (b, f, i, l, m, q, s), (b, f, i, l, m, q, t), (b, f, i, l, m, r, s), (b, f, i, l, m, r, t), (b, f, i, l, n, p, s), (b, f, i, l, n, p, t), (b, f, i, l, n, q, s), (b, f, i, l, n, q, t), (b, f, i, l, n, r, s), (b, f, i, l, n, r, t), (b, f, i, l, o, p, s), (b, f, i, l, o, p, t), (b, f, i, l, o, q, s), (b, f, i, l, o, q, t), (b, f, i, l, o, r, s), (b, f, i, l, o, r, t), (c, d, g, j, m, p, s), (c, d, g, j, m, p, t), (c, d, g, j, m, q, s), (c, d, g, j, m, q, t), (c, d, g, j, m, r, s), (c, d, g, j, m, r, t), (c, d, g, j, n, p, s), (c, d, g, j, n, p, t), (c, d, g, j, n, q, s), (c, d, g, j, n, q, t), (c, d, g, j, n, r, s), (c, d, g, j, n, r, t), (c, d, g, j, o, p, s), (c, d, g, j, o, p, t), (c, g, j, o, q, s), (c, g, j, o, q, t), (c, d, g, j, o, r, s), (c, d, g, j, o, r, t), (c, d, g, k, m, p, s), (c, d, g, k, m, p, t), (c, d, g, k, m, q, s), (c, d, g, k, m, q, t), (c, d, g, k, m, r, s), (c, d, g, k, m, r, t), (c, d, g, k, n, p, s), (c, d, g, k, n, p, t), (c, d, g, k, n, q, s), (c, d, g, k, n, q, t), (c, d, g, k, n, r, s), (c, d, g, k, n, r, t), (c, d, g, k, o, p, s), (c, d, g, k, o, p, t), (c, d, g, k, o, q, s), (c, d, g, k, o, q, t), (c, d, g, k, o, r, s), (c, d, g, k, o, r, t), (c, d, g, l, m, p, s), (c, d, g, l, m, p, t), (c, d, g, l, m, q, s), (c, d, g, l, m, q, t), (c, d, g, l, m, r, s), (c, d, g, l, m, r, t), (c, d, g, l, n, p, s), (c, d, g, l, n, p, t), (c, d, g, l, n, q, s), (c, d, g, l, n, q, t), (c, d, g, l, n, r, s), (c, d, g, l, n, r, t), (c, d, g, l, o, p, s), (c, d, g, l, o, p, t), (c, d, g, l, o, q, s), (c, d, g, l, o, q, t), (c, d, g, l, o, r, s), (c, d, g, l, o, r, t), (c, d, h, j, m, p, s), (c, d, h, j, m, p, t), (c, d, h, j, m, q, s), (c, d, h, j, m, q, t), (c, d, h, j, m, r, s), (c, d, h, j, m, r, t), (c, d, h, j, n, p, s), (c, d, h, j, n, p, t), (c, d, h, j, n, q, s), (c, d, h, j, n, q, t), (c, d, h, j, n, r, s), (c, d, h, j, n, r, t), (c, d, h, j, o, p, s), (c, d, j, o, p, t), (c, d, h, j, o, q, t), (c, d, h, j, o, r, s), (c, d, h, j, o, r, t), (c, d, h, k, m, p, s), (c, d, h, k, m, p, t), (c, d, h, k, m, q, s), (c, d, h, k, m, q, t), (c, d, h, k, m, r, s), (c, d, h, k, m, r, t), (c, d, h, k, n, p, s), (c, d, h, k, n, p, t), (c, d, h, k, n, q, s), (c, d, h, k, n, q, t), (c, d, h, k, n, r, s), (c, d, h, k, n, r, t), (c, d, h, k, o, p, s), (c, d, h, k, o, p, t), (c, d, h, k, o, q, s), (c, d, h, k, o, q, t), (c, d, h, k, o, r, s), (c, d, h, k, o, r, t), (c, d, h, l, m, p, s), (c, d, h, l, m, p, t), (c, d, h, l, m, q, s), (c, d, h, l, m, q, t), (c, d, h, l, m, r, s), (c, d, h, l, m, r, t), (c, d, h, l, n, p, s), (c, d, h, l, n, p, t), (c, d, h, l, n, q, s), (c, d, h, l, n, q, t), (c, d, h, l, n, r, s), (c, d, h, l, n, r, t), (c, d, h, l, o, p, s), (c, d, h, l, o, p, t), (c, d, h, l, o, q, s), (c, d, h, l, o, q, t), (c, d, h, l, o, r, s), (c, d, h, l, o, r, t), (c, d, j, m, p, s), (c, d, i, j, m, p, t), (c, d, i, j, m, q, s), (c, d, i, j, m, q, t), (c, d, i, j, m, r, s), (c, d, i, j, m, r, t), (c, d, i, j, n, p, s), (c, d, i, j, n, p, t), (c, d, i, j, n, q, s), (c, d, i, j, n, q, t), (c, d, i, j, n, r, s), (c, d, i, j, n, r, t), (c, d, i, j, o, p, s), (c, d, i, j, o, p, t), (c, d, i, j, o, q, s), (c, d, i, j, a, q, t), (c, d, i, j, o, r, s), (c, d, i, j, o, r, t), (c, d, i, k, m, p, s), (c, d, i, k, m, p, t), (c, d, i, k, m, q, s), (c, d, i, k, m, q, t), (c, d, i, k, m, r, s), (c, d, i, k, m, r, t), (c, d, i, k, n, p, s), (c, d, i, k, n, p, t), (c, d, i, k, n, q, s), (c, d, i, k, n, q, t), (c, d, i, k, n, r, s), (c, d, i, k, n, r, t), (c, d, i, k, o, p, s), (c, d, i, k, o, p, t), (c, d, i, k, o, q, s), (c, d, i, k, o, q, t), (c, d, i, k, o, r, s), (c, d, i, k, o, r, t), (c, d, i, l, m, p, s), (c, d, i, l, m, p, t), (c, d, i, l, m, q, s), (c, d, i, l, m, q, t), (c, d, i, l, m, r, s), (c, d, i, l, m, r, t), (c, d, i, l, n, p, s), (c, d, i, l, n, p, t), (c, d, i, l, n, q, s), (c, d, i, l, n, q, t), (c, d, i, l, n, r, s), (c, d, i, l, n, r, t), (c, d, i, l, o, p, s), (c, d, i, l, o, p, t), (c, d, i, l, o, q, s), (c, d, i, l, o, q, t), (c, d, i, l, o, r, s), (c, d, i, o, r, t), (c, e, g, j, m, p, s), (c, e, g, j, m, p, t), (c, e, g, j, m, q, s), (c, e, g, j, m, q, t), (c, e, g, j, m, r, s), (c, e, g, j, m, r, t), (c, e, g, j, n, p, s), (c, e, g, j, n, p, t), (c, e, g, j, n, q, s), (c, e, g, j, n, q, t), (c, e, g, j, n, r, s), (c, e, g, j, n, r, t), (c, e, g, j, o, p, s), (c, e, g, j, o, p, t), (c, e, g, j, o, q, s), (c, e, g, j, o, q, t), (c, e, g, j, o, r, s), (c, e, g, j, o, r, t), (c, e, g, k, m, p, s), (c, e, g, k, m, p, t), (c, e, g, k, m, q, s), (c, e, g, k, m, q, t), (c, e, g, k, m, r, s), (c, e, g, k, m, r, t), (c, e, g, k, n, p, s), (c, e, g, k, n, p, t), (c, e, g, k, n, q, s), (c, e, g, k, n, q, t), (c, e, g, k, n, r, s), (c, e, g, k, n, r, t), (c, e, g, k, o, p, s), (c, e, g, k, o, p, t), (c, e, g, k, o, q, s), (c, e, g, k, o, q, t), (c, e, g, k, o, r, s), (c, e, g, k, o, r, t), (c, e, g, l, m, p, s), (c, e, g, l, m, p, t), (c, e, g, l, m, q, s), (c, e, g, l, m, q, t), (c, e, g, l, m, r, s), (c, e, g, l, m, r, t), (c, e, g, l, n, p, s), (c, e, g, l, n, p, t), (c, e, g, l, n, q, s), (c, e, g, l, n, q, t), (c, e, g, l, n, r, s), (c, e, g, l, n, r, t), (c, e, g, l, o, p, s), (c, e, g, l, o, p, t), (c, e, g, l, o, q, s), (c, e, g, l, o, q, t), (c, e, g, l, o, r, s), (c, e, g, l, o, r, t), (c, e, h, j, m, p, s), (c, e, h, j, m, p, t), (c, e, h, j, m, q, s), (c, e, h, j, m, q, t), (c, e, h, j, m, r, s), (c, e, h, j, m, r, t), (c, e, h, j, n, p, s), (c, e, h, j, n, p, t), (c, e, h, j, n, q, s), (c, e, h, j, n, q, t), (c, e, h, j, n, r, s), (c, e, h, j, n, r, t), (c, e, h, j, o, p, s), (c, e, h, j, o, p, t), (c, e, h, j, o, q, s), (c, e, h, j, o, q, t), (c, e, h, j, o, r, s), (c, e, h, j, o, r, t), (c, e, h, k, m, p, s), (c, e, h, k, m, p, t), (c, e, h, k, m, q, s), (c, e, h, k, m, q, t), (c, e, h, k, m, r, s), (c, e, h, k, m, r, t), (c, e, h, k, n, p, s), (c, e, h, k, n, p, t), (c, e, h, k, n, q, s), (c, e, h, k, n, q, t), (c, e, h, k, n, r, s), (c, e, h, k, n, r, t), (c, e, h, k, o, p, s), (c, e, h, k, o, p, t), (c, e, h, k, o, q, s), (c, e, h, k, o, q, t), (c, e, h, k, o, r, s), (c, e, h, k, o, r, t), (c, e, h, l, m, p, s), (c, e, h, l, m, p, t), (c, e, h, l, m, q, s), (c, e, h, l, m, q, t), (c, e, h, l, m, r, s), (c, e, h, l, m, r, t), (c, e, h, l, n, p, s), (c, e, h, l, n, p, t), (c, e, h, l, n, q, s), (c, h, l, n, q, t), (c, e, h, l, n, r, s), (c, e, h, l, n, r, t), (c, e, h, l, o, p, s), (c, e, h, l, o, p, t), (c, e, h, l, o, q, s), (c, e, h, l, o, q, t), (c, e, h, l, o, q, t), (c, e, h, l, o, r, t), (c, e, i, j, m, p, s), (c, e, i, j, m, p, t), (c, e, i, j, m, q, s), (c, e, i, j, m, q, t), (c, e, i, j, m, r, s), (c, e, i, j, m, r, t), (c, e, i, j, n, p, s), (c, e, i, j, n, p, t), (c, e, i, j, n, q, s), (c, e, i, j, n, q, t), (c, e, i, j, n, r, s), (c, e, i, j, n, r, t), (c, e, i, j, o, p, s), (c, e, i, j, o, p, t), (c, e, i, j, o, q, s), (c, e, i, j, o, q, t), (c, e, i, j, o, r, s), (c, e, i, j, o, r, t), (c, e, i, k, m, p, s), (c, e, i, k, m, p, t), (c, e, i, k, m, q, s), (c, e, i, k, m, q, t), (c, e, i, k, m, r, s), (c, e, i, k, m, r, t), (c, e, i, k, n, p, s), (c, e, i, k, n, p, t), (c, e, i, k, n, q, s), (c, e, i, k, n, q, t), (c, e, i, k, n, r, s), (c, e, i, k, n, r, t), (c, e, i, k, o, p, s), (c, e, i, k, o, p, t), (c, e, i, k, o, q, s), (c, e, i, k, o, q, t), (c, e, i, k, o, r, s), (c, e, i, k, o, r, t), (c, e, i, l, m, p, s), (c, e, i, l, m, p, t), (c, e, i, l, m, q, s), (c, e, i, l, m, q, t), (c, e, i, l, m, r, s), (c, e, i, l, m, r, t), (c, e, i, l, n, p, s), (c, e, i, l, n, p, t), (c, e, i, l, n, q, s), (c, e, i, l, n, q, t), (c, e, i, l, n, r, s), (c, e, i, l, n, r, t), (c, e, i, l, o, p, s), (c, e, i, o, p, t), (c, e, i, l, o, q, s), (c, e, i, l, o, q, t), (c, e, i, l, o, r, s), (c, e, i, l, o, r, t), (c, f, g, j, m, p, s), (c, f, g, j, m, p, t), (c, f, g, j, m, q, s), (c, f, g, j, m, q, t), (c, f, g, j, m, r, s), (c, f, g, j, m, r, t), (c, f, g, j, n, p, s), (c, f, g, j, n, p, t), (c, f, g, j, n, q, s), (c, f, g, j, n, q, t), (c, f, g, j, n, r, s), (c, f, g, j, n, r, t), (c, f, g, j, o, p, s), (c, f, g, j, o, p, t), (c, f, g, j, o, q, s), (c, f, g, j, o, q, t), (c, f, g, j, o, r, s), (c, f, g, j, o, r, t), (c, f, g, k, m, p, s), (c, f, g, k, m, p, t), (c, f, g, k, m, q, s), (c, f, g, k, m, q, t), (c, f, g, k, m, r, s), (c, f, g, k, m, r, t), (c, f, g, k, n, p, s), (c, f, g, k, n, p, t), (c, f, g, k, n, q, s), (c, f, g, k, n, q, t), (c, f, g, k, n, r, s), (c, f, g, k, n, r, t), (c, f, g, k, o, p, s), (c, f, g, k, o, p, t), (c, f, g, k, o, q, s), (c, f, g, k, o, q, t), (c, f, g, k, o, r, s), (c, f, g, k, o, r, t), (c, f, g, l, m, p, s), (c, f, g, l, m, p, t), (c, f, g, l, m, q, s), (c, f, g, l, m, q, t), (c, f, g, l, m, r, s), (c, f, g, l, m, r, t), (c, f, g, l, n, p, s), (c, f, g, l, n, p, t), (c, f, g, l, n, q, s), (c, f, g, l, n, q, t), (c, f, g, l, n, r, s), (c, f, g, l, n, r, t), (c, f, g, l, o, p, s), (c, f, g, l, o, p, t), (c, f, g, l, o, q, s), (c, f, g, t, o, q, t), (e, f, g, l, o, r, s), (c, f, g, l, o, r, t), (c, f, h, j, m, p, s), (c, f, h, j, m, p, t), (c, f, h, j, m, q, s), (c, f, h, j, m, q, t), (c, f, h, j, m, r, s), (c, f, h, j, m, r, t), (c, f, h, j, n, p, s), (c, f, h, j, n, p, t), (c, f, h, j, n, q, s), (c, f, h, j, n, q, t), (c, f, h, j, n, r, s), (c, f, h, j, n, r, t), (c, f, h, j, o, p, s), (c, f, h, j, o, p, t), (c, f, h, j, o, q, s), (c, f, h, j, o, q, t), (c, f, h, j, o, r, s), (c, f, h, j, o, r, t), (c, f, h, k, m, p, s), (c, f, h, k, m, p, t), (c, f, h, k, m, q, s), (c, f, h, k, m, q, t), (c, f, h, k, m, r, s), (c, f, h, k, m, r, t), (c, f, h, k, n, p, s), (c, f, h, k, n, p, t), (c, f, h, k, n, q, s), (c, f, h, k, n, q, t), (c, f, h, k, n, r, s), (c, f, h, k, n, r, t), (c, f, h, k, o, p, s), (c, f, h, k, o, p, t), (c, f, h, k, o, q, s), (c, f, h, k, o, q, t), (c, f, h, k, o, r, s), (c, f, h, k, o, r, t), (c, f, h, l, m, p, s), (c, f, h, l, m, p, t), (c, f, h, l, m, q, s), (c, f, h, l, m, q, t), (c, f, h, l, m, r, s), (c, f, h, l, m, r, t), (c, f, h, l, n, p, s), (c, f, h, l, n, p, t), (c, f, h, l, n, q, s), (c, f, h, l, n, q, t), (c, f, h, l, n, r, s), (c, f, h, l, n, r, t), (c, f, h, l, o, p, s), (c, f, h, l, o, p, t), (c, f, h, l, o, q, s), (c, f, h, l, o, q, t), (c, f, h, l, o, r, s), (c, f, h, l, o, r, t), (c, f, i, j, m, p, s), (c, f, i, j, m, p, t), (c, f, i, j, m, q, s), (c, f, i, j, m, q, t), (c, f, i, j, m, r, s), (c, f, i, j, m, r, t), (c, f, i, j, n, p, s), (c, f, i, j, n, p, t), (c, f, i, j, n, q, s), (c, f, i, j, n, q, t), (c, f, i, j, n, r, s), (c, f, i, j, n, r, t), (c, f, i, j, o, p, s), (c, f, i, j, o, p, t), (c, f, i, j, o, q, s), (c, f, i, j, o, q, t), (c, f, i, j, o, r, s), (c, f, i, j, o, r, t), (c, f, i, k, m, p, s), (c, f, i, k, m, p, t), (c, f, i, k, m, q, s), (c, f, i, k, m, q, t), (c, f, i, k, m, r, s), (c, f, i, k, m, r, t), (c, f, i, k, n, p, s), (c, f, i, k, n, p, t), (c, f, i, k, n, q, s), (c, f, i, k, n, q, t), (c, f, i, k, n, r, s), (c, f, i, k, n, r, t), (c, f, i, k, o, p, s), (c, f, i, k, o, p, t), (c, f, i, k, o, q, s), (c, f, i, k, o, q, t), (c, f, i, k, o, r, s), (c, f, i, k, o, r, t), (c, f, i, l, m, p, s), (c, f, i, l, m, p, t), (c, f, i, l, m, q, s), (c, f, i, l, m, q, t), (c, f, i, l, m, r, s), (c, f, i, l, m, r, t), (c, f, i, l, n, p, s), (c, f, i, l, n, p, t), (c, f, i, l, n, q, s), (c, f, i, l, n, q, t), (c, f, i, l, n, r, s), (c, f, i, l, n, r, t), (c, f, i, l, o, p, s), (c, f, i, l, o, p, t), (c, f, i, l, o, q, s), (c, f, i, l, o, q, t), (c, f, i, l, o, r, s), (c, f, i, l, o, r, t).

The present invention tablet has excellent light-stability as shown in the examples mentioned later. In spite of high content of the main ingredient, the tablet is compact, sufficiently hard and readily administrable.

The dosage varies with the conditions of the patients, administration route, their age, and body weight. In the case of oral administration, the dosage is thought to be preferable between about 1200 mg to about 1800 mg per a day. The amount per one administration is between 400 mg to 600 mg because of three division a day, and it is preferable to take two tablets each containing the main ingredient of between 200 mg to 300 mg.

The following examples and test examples are provided to further illustrate the present invention and are not to be construed as limiting the scope thereof.

EXAMPLE

Example 1

Preparation of Pirfenidone Tablets

Pirfenidone (2,000 g) was mixed with 560 g of lactose and 50 g of carmellose calcium. The mixture was granulated by spraying a 5 (W/W) % aqueous solution of hydroxypropylcellulose (60 g) with a fluid bed granulator. Carmellose calcium and magnesium stearate were added to the granules at the ratios of 5.6 and 1.1 wt. % to the weight of the granules, respectively. The obtained mixture was compressed at a force of 13 kN and to give plain pirfenidone tablets each containing 200 mg of pirfenidone (size: 12.0× 6.0 mm, weight: 285 mg/tablet).

The plain tablets were coated by spraying a 10 wt. % aqueous solution containing hydroxypropylmethylcellulose (66.7 g), triethyl citrate (6.7 g), and titanium oxide 26.6 g in an amount of 10 mg per tablet with a High-coator, to give the objective pirfenidone tablets.

The components of a pirfenidone tablet is shown below.

TABLE 1

| Component | Amount | Note |
| --- | --- | --- |
| Pirfenidone | 200.0 mg | |
| Lactose | 56.0 mg | |
| Carmellose calcium | 20.0 mg | Intra-granular: 5.0 mg |
| | | Extera-granular 15.0 mg |
| Hydroxypropylcellulose | 6.0 mg | |
| Magnesium stearate | 3.0 mg | |
| Total of weight of a plain tablet | 285.0 mg | |
| Hydroxypropylmethylcellulose 2910 | 6.67 mg | |
| Titanium oxide | 2.66 mg | |
| Triethyl citrate | 0.67 mg | |
| Magnesium stearate | trace | 0.02 mg |
| Talc | trace | 0.02 mg |
| Total weight of coating | 10.00 mg | |
| Total weight of a coated tablet | 295.0 mg | |

Example 2

Light Exposure Testing

Light exposure test of pirfenidone was carried out under the following condition, using "drug substance" obtained by packing 500 mg of milled pirfenidone drug substance in a heat-sealed transparent SP (Striped Package), "compressed drug substance" obtained by statically compressing 300 mg of milled pirfenidone drug substance, "the plain tablets" obtained in the above Example 1, and "the coated tablets" obtained in the above Example 1. The results are shown in table 2.

(Test Condition)
light irradiation apparatus: light stability test apparatus (LTL400-D5) (Nagano Science Equipment Mfg. Co., Ltd.)
fluorescent light: D65 fluorescent lamp for color comparing and test
temperature and humidity: 25° C., room humidity
illumination intensity: 3570 Lx
exposure dose: 1,200,000 Lx·hr
coloring difference measure apparatus: Color analyzer TC-1800MK-II
measurement method: reflected ray measurement
color specification system: CIELAB
measurement condition: second degree visual field
standard light: C

TABLE 2

| Sample | Color difference (ΔE) | Discoloration |
|---|---|---|
| Drug substance | 0.73 | slight |
| Compressed drug substance | 3.62 | remarkable |
| Plain tablets | 5.08 | remarkable |
| Coated tablets | 0.75 | slight |

Table 2 showed that remarkable color difference was not observed in the case of the pirfenidone drug substance, but a pirfenidone compressed drug substance and a pirfenidone plain tablet have a problem in light-stability. However, a pirfenidone coated tablet solves the problem in light-stability. A pirfenidone coated tablet is confirmed to have no problem in odor or bitterness.

INDUSTRIAL APPLICABILITY

The present invention provides a compact and sufficiently hard tablet containing a high content of pirfenidone which is necessary to be administered in high dose. And at the same time, the present invention solves the problem of its odor or bitterness and provides a readily administrable tablet. Furthermore, it solves the problem of light-stability caused by tableting pirfenidone and provides the stability requested as a medicine.

The invention claimed is:

1. A coated dosage form comprising a compressed tablet comprising 5-methyl-1-phenyl-2-(1H)-pyridone as an active ingredient; and a coating comprising a light shielding agent disposed on the compressed tablet.

2. The dosage form of claim 1, wherein the light shielding agent is selected from the group consisting of titanium oxide, ferric oxide, and any mixture thereof.

3. The dosage form of claim 1, wherein the light-shielding agent is present in an amount ranging from 0.05 to 3 wt % based on the weight of the active ingredient.

4. The dosage form of claim 1, wherein the coating further comprises a coating basis.

5. The dosage form of claim 4, wherein the coating basis is selected from the group consisting of hydroxypropylmethylcellulose, hydroxypropylcellulose, and any mixture thereof.

6. The dosage form of claim 4, wherein the coating basis is 2 to 6 wt % based on the weight of the active ingredient.

7. The dosage form of claim 1, wherein the coating further comprises 0.01 to 1 wt % plasticizer based on the weight of the active ingredient.

8. The dosage form of claim 7, wherein the plasticizer is selected from the group consisting of triethyl citrate, triacetin, and any mixture thereof.

9. The dosage form of claim 1, wherein the amount of 5-methyl-1-phenyl-2-(1H)-pyridone is about 200 mg to 400 mg.

10. The dosage form of claim 1, wherein the active ingredient comprises 50 to 85 wt % based on the weight of the dosage form.

11. The dosage form of claim 1, comprising intragranular and extragranular components, wherein the intragranular component comprises the 5-methyl-1-phenyl-2-(1H)-pyridone and the extragranular component comprises a disintegrator.

12. The dosage form of claim 11, wherein the disintegrator is selected from the group consisting of carmellose calcium, carmellose sodium, croscarmellose sodium, low substituted hydroxypropylcellulose, cross-linked polyvinylpyrrolidone, and any mixture thereof.

13. The dosage form of claim 11, wherein the disintegrator is provided in an amount of 5 to 40 wt % based on the weight of the active ingredient.

14. The dosage form of claim 11, wherein the intragranular component further comprises an excipient and a binder.

15. The dosage form of claim 14, wherein the excipient is selected from the group consisting of lactose, corn starch, crystalline cellulose, and any mixture thereof.

16. The dosage form of claim 14, wherein the binder is selected from the group consisting of hydroxypropylcellulose, polyvinylpyrrolidone, and any mixture thereof.

17. The dosage form of claim 11, wherein the extragranular component further comprises a lubricant.

18. The dosage form of claim 17, wherein the lubricant is selected from the group consisting of magnesium stearate, talc, and any mixture thereof.

19. The dosage form of claim 18, wherein the lubricant is included in an amount of 0.5 to 5 wt % based on the weight of the active ingredient.

20. The dosage form of claim 1, further comprising an excipient, a disintegrator, a binder, and a lubricant.

* * * * *